(12) United States Patent
Klein

(10) Patent No.: US 6,168,799 B1
(45) Date of Patent: Jan. 2, 2001

(54) β-D-GLUCAN TOPICAL COMPOSITION

(75) Inventor: Barbara K. Klein, Lindstrom, MN (US)

(73) Assignee: Brennen Medical, Inc., St. Paul, MN (US)

( * ) Notice: Under 35 U.S.C. 154(b), the term of this patent shall be extended for 0 days.

(21) Appl. No.: 09/231,311

(22) Filed: Jan. 13, 1999

Related U.S. Application Data

(63) Continuation of application No. 08/957,529, filed on Oct. 24, 1997, now Pat. No. 5,980,918.

(51) Int. Cl.⁷ .............................. A61K 7/00; A61K 7/06; A61K 7/42; A61K 31/70; A61K 31/715
(52) U.S. Cl. ........................... 424/401; 424/70.1; 424/59; 514/35; 514/53; 514/54; 514/847
(58) Field of Search ................................... 424/401, 70.1, 424/59; 514/847, 53, 54, 35

(56) References Cited

U.S. PATENT DOCUMENTS 5,573,785  *  11/1996  Murphy ............................... 424/70.1
5,783,569  *   7/1998  Jamas et al. ........................... 514/54

OTHER PUBLICATIONS

Estrada et al, Immunomodulatory activities of oat beta glucan in vitro and in vivo, Biosis (AN 128:191445, 1997.*

Osborne, Method and composition for cleaning wounds—comprises irrigating the wound with a surfactant, an antiseptic preservative mixed in an aqueous solution having minimal cytotoxity, WPIDS (97–489402 (45)), 1997.*

Osborne, Topical bactericidal composition, eg for wound cleansing containing essential oil distilled from Schinus Molle L. tree, effective e.g. agiainst *Pseudomonas aeruginosa*, (WPIDS AN 96–200652 )28)), 1996.*

Camano, Topical bactericidal composition e.g. for wound cleandsing containing—essential oil distilled, (WPIDS AN 97–309779 (28)), 1997.*

* cited by examiner

*Primary Examiner*—Theodore J. Criares
(74) *Attorney, Agent, or Firm*—Moore & Hansen

(57) ABSTRACT

A topical composition for healing treatment of burns and wounds and scarring therefrom has as the active ingredient cereal-derived (1-3) (1-4) β-D-glucan at about 0.5–15 w/w percent. The composition may be formulated in various forms with creams and gels being preferred for application to the skin.

8 Claims, 1 Drawing Sheet

β-D-GLUCAN TOPICAL COMPOSITION

This is a continuation of application Ser. No. 08/957,529, filed Oct. 24, 1997 now U.S. Pat. No. 5,980,918.

BACKGROUND OF THE INVENTION

1. Field of the Invention

This invention relates generally to topical compositions for the treatment of superficial and partial thickness burns and wounds of the skin and mucosa. More particularly, the invention pertains to formulations of topical creams and gels providing cleansing, moisturizing, soothing and anti-pruritic activity for topical therapeutic treatment of wounds and burns and other skin loss injuries and conditions.

2. State of the Art

A group of complex polysaccharides known as glucans are found in the cell walls of yeast and bacteria. Though the structures of the microbial-derived glucans have not been completely elucidated, they are known to include long-chain carbohydrate polymers composed solely of β-D-glucan residues with 1,3 linkages or a combination of 1,3- and 1,6-linkages. In the cell walls of the yeast *Saccharomyces cerevisiae,* the glucans may also be associated with mannan, another complex polysaccharide.

Studies have indicated that yeast-derived 1,3-glucan activates macrophages, including phages with immunological activity against tumor growth. The 1,6-glucans were found to be inactive relative to macrophages. Such is reported by Di Luzio et al. in THE MACROPHAGE IN NEOPLASIA, Mary A. Fink, editor, 1976, Academic Press, New York, pp 181–182.

In U.S. Pat. No. 5,158,772 of Davis, the incorporation of a microbial-derived beta-1,3-glucan-type polysaccharide in a topical composition is disclosed. The polysaccharide is produced by a bacterial microorganism known as *Cellulomonas flavigena.* The functions of the polysaccharide in the topical composition are described as three-fold, i.e. (a) its effectiveness as a water-holding agent by which it controls the fluidity, appearance and "feel" of a composition, (b) its viscosity raising effect, and (c) its ability to suspend other cosmetic and therapeutic agents such as dyes, drugs, germicides, anesthetics, etc. as a carrier.

In a U.S. patent application of Williams and Lawin, bearing Ser. No. 08/423,838 and commonly assigned with this application, a mesh matrix wound dressing is disclosed which incorporates cereal-derived β-D-glucan and collagen in a cast burn dressing.

A topical healing unguent is needed for treatment of burns and wounds of the skin and mucosa where a wound dressing is not indicated.

SUMMARY OF THE INVENTION

The invention comprises a multi-purpose topical composition for application to the skin and mucosa. It is intended for use as a topically applied cream or gel to provide cleansing and soothing relief of superficial and partial thickness burns, as a moisturizer to enhance water retention of the stratum corneum, and to relieve the itching associated with hypertrophic or keloid scarring.

The active ingredient of the topical composition of the invention is being investigated as a possible biological response modifier and macrophage stimulant.

The primary active component of the topical composition is cereal-derived β-D-Glucan, chemically comprising a large number of glucopyranosyl units determined to be linked by (1-3) and (1-4) linkages. The preferred active agent is β-D-Glucan derived from oats, although the glucans from barley, wheat and/or other cereal grains may be used for the topical composition, provided the (1-4) (1-3) β-D-Glucan can be extracted economically.

As generally formulated, the composition of the topical cream of the invention comprises the following, where the indicated concentration of each component is uniformly given as a percentage of the total of all components:

| | |
|---|---|
| cereal-derived β-D-Glucan (active agent) | about 0.5–15 w/w % |
| ointment base | about 10–20 w/w % |
| humectant(s) | about 2–6 w/w % |
| suspending/viscosity increasing agent(s) | about 0.01–8.0 w/w % |
| stiffening agent(s) | about 0.5–6 w/w % |
| emulsifying/solubilizing agent(s) | about 0.1–8 w/w % |
| antimicrobial agent(s) | about 0.1–2 w/w % |
| plasticizer(s) | about 5–15 w/w % |
| solvent(s) | balance |

Some ingredients may have several functions. For example, glycerol may serve both as a solvent and a plasticizer, and propylene glycol may serve as a solvent, humectant and plasticizer.

A general formulation for a gel composition of the invention is:

| | |
|---|---|
| cereal derived β-D-Glucan (active agent) | about 0.5–15 w/w % |
| water | about 80–98 w/w % |
| suspending/viscosity increasing agent(s) | about 0.5–8 w/w % |
| emulsifying/solubilizing agent(s) | about 0–5 w/w % |
| antimicrobial agent(s) | about 0.05–1 w/w % |

The cereal-derived β-D-Glucan in this composition is significantly different from glucans obtained from other sources, including β-D-Glucans derived from yeast such as *Saccharomyces cerevisiae* and bacteria such as *Cellulomonas flavigena.*

The primary source of β-Glucan has historically been yeast and bacterial cells. However, the cereal-derived (1-4) (1-3) β-D-glucan useful in the invention is distinctive from microbial-derived glucans which have all (1-3) linkages or primarily (1-3) linkages with a few (1-6) linkages. The molecular weight of the mixed-linkage cereal-derived β-D-Glucan used in this invention is much greater than that of the microbial-derived glucans.

DETAILED DESCRIPTION OF THE INVENTION

In accordance with the invention, new compositions for multi-purpose topical treatment are presented wherein the active ingredient is a cereal-derived β-D-glucan, identified herein as "CDG". The invention pertains to various topical compositions including a solvent base varying from essentially all water to essentially all oil. The invention includes topical compositions variously known as unguents, creams, gels, emollients, lotions and oils, each with a generally characteristic solvent composition, and having a form ranging from liquid to semisolid.

Compounds classified as β-glucans comprise a large group of high molecular weight polymers containing glucopyranosyl units in β-linked chains. β-glucans are found in essentially all living cells which are enclosed by cell walls, with considerable structural variation dependent on source. They are highly unbranched homopolysaccharides and isomerically diaposed to alpha-D-glucan (e.g. starch) which is typically non-functional as a structural support component of the cell.

Figure 1:
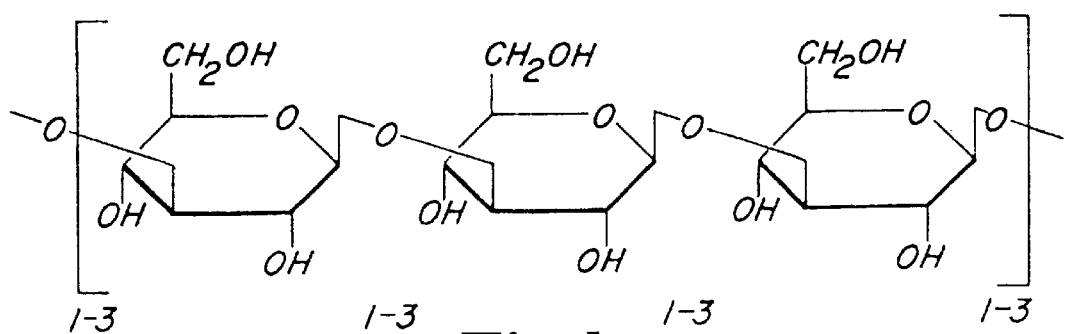
FIG. 1 is a drawing of a generallized chemical structure of microbe-derived (1-3) β-D-glucan used in a prior art composition.
Figure 2:
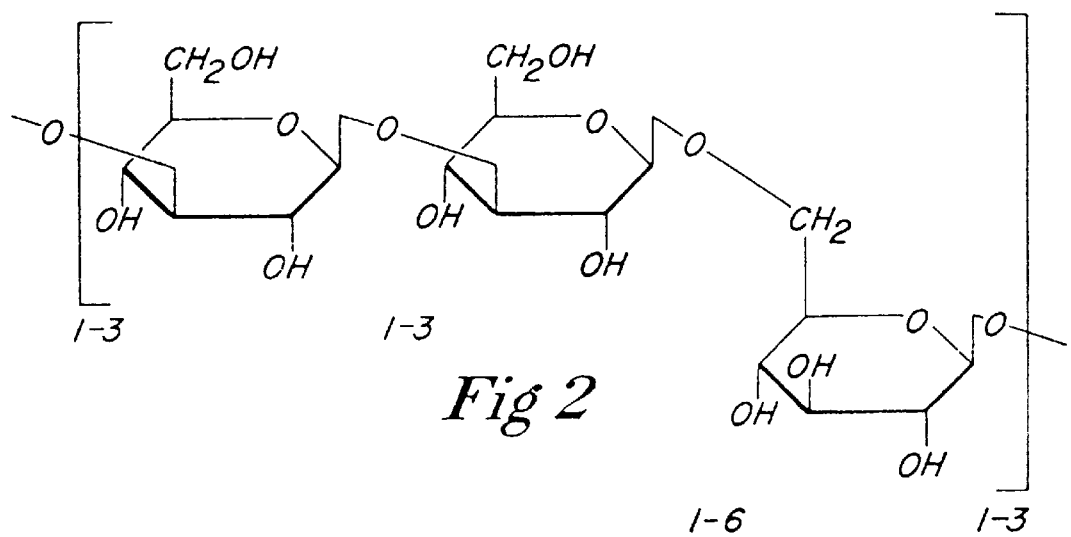
FIG. 2 is a drawing of a generallized chemical structure of microbe-derived (1-3)(1-6) β-D-glucan.

As depicted in FIG. 1, glucans derived from microbes have been generally characterized as essentially comprising (1-3)-linked chains of glucopyranosyl units. With the recent advances in test identification methods, yeast-derived glucans having primarily (1-3)-linkages with a relatively small number of (1-6)-linkages (FIG. 2) have been identified. Yeast-derived glucan polymers are often associated with mannose, and typically have a helically coiled chain shape.

Figure 3:
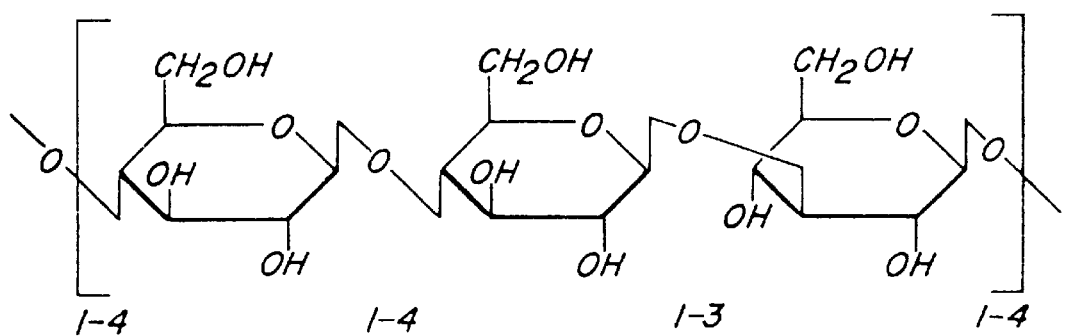
FIG. 3 is a drawing of a proposed generallized chemical structure of mixed-linkage cereal-derived (1-3)(1-4) β-D-glucan used in a topical composition of the invention.

The mixed linkage glucan polymers found in cereals are quite different from yeast-derived and bacteria-derived polymers. Glucans derived from cereal grains, as shown in FIG. 3, have (1-3) and (1-4) linkages and generally have a linear or kinked linear chain.

Cereal-derived glucan (CDG) may be characterized as follows:
  a. CDG is a long chain, unbranched polysaccharide which typically comprises about 3–4 percent of oat and barley grains. The CDG concentration is greater, e.g. 7–10 percent, in the milled bran fraction of oats.
  b. CDG is found in the endosperm and aleurone cell walls of most cereal grains. The microbe-derived glucans occur in the cell wall of the yeast or bacteria.
  c. CDG is a mixed-linkage molecule containing about 70 percent (1-4)-linkages and about 30 percent (1-3)-linkages. The (1-3)-linked units mostly occur singly whereas the (1-4)-linked units typically occur in groups of three or four glucopyranosyl units. Thus, the resultant structure is a series of short runs of 3 or 4 (1-4)-linked glucopyranosyl units, adjacent runs connected by (1-3) linkages. The frequencies of the groups of three 20 (cellotriosyl) and four (cellotetraosyl) glucopyranosyl units also tend to be characteristic of the source, being affected by cereal variety, tissue age, and stage of maturity oat-derived CDG typically has more of the groups of three consecutive (1-4)-linked glucopyranosyl units than does barley-derived CDG. The ratio of trisaccharide to tetrasaccharide groups is about 2:1 for oats and closer to 3:1 for barley. CDG differs from microbe-derived glucans, which have all (1-3)-linkages or mostly (1-3)-linkages with some (1-6)-linkages.
  d. CDG is a linear molecule, while yeast-derived glucan forms a helical shape.
  e. The degree of polymerization of CDG is in the range of about 1200–1800. On the other hand, yeast-derived β-D-glucan has a much lower degree of polymerization, i.e. about 60–80. Cellulose, the primary constituent of plant cell walls, has all β (1-4) linkages and a degree of polymerization of about 10,000 to 15,000.
  f. CDG forms viscous solutions in warm water. On the other hand, yeast-derived glucan is insoluble in water but dispersible in aqueous systems.
  g. CDG occurs within the grain with a fairly broad range of MW, i.e. about 200,000 to 700,000. The molecular weight is believed to be dependent upon the grain species, grain source, glucan extraction conditions and particular laboratory. Microbe-derived glucan has a much lower molecular weight, in the range of about 10,000 to 14,000. Cellulose has a molecular weight of about 700,000.
  h. The use of CDG as a food component has been studied extensively by various researchers; studies have included the use of CDG in regulation of glucose metabolism, hypoglycemic response, reduction in serum cholesterol, and the like.

Thus, in terms of chemical structure and molecular weight, CDG is much more like cellulose than are the microbial-derived glucans.

Each of the components of the new composition serves a particular function or functions, and is available in purities conducive to use in the particular applications. Thus, a component may comprise United States Pharmacia (USP), National Formulary (NF), or other purified grade appropriate for topical use on burns and wounds on the skin.

In addition to cereal-derived β-D-glucan, the components of the cream formulation include:
  a. an ointment base, preferably white petrolatum. An alternative but somewhat less desirable substance for this purpose is lanolin.
  b. a solvent, primarily or entirely water. Additional solvents which may be added at generally lower concentrations include natural oils such as cod liver oil, mineral oil, etc., and glycerol or propylene glycol. The water content of the cream formulation is at least about 50 percent.
  c. a plasticizer, preferably glycerol. Propylene glycol or another glycol may also be used as a plasticizer.
  d. a humectant, preferably propylene glycol.
  e. a suspending or viscosity enhancement agent, such as carrageenen. Other possible exemplary agents include polyvinyl alcohol, xanthan gum, agarose, alginate, guar gum, Carbopol 940™ carbomer (B.F. Goodrich), and carboxymethylcellulose (CMC), as well as mixtures thereof. A variation in the concentration of suspending agents is compensated by varying the water (solvent) concentration.
  f. an emulsifying or solubilizing agent or agents. Exemplary agents are sodium lauryl sulfate and triethanolamine. In the preferred formulation, a combination of sodium lauryl sulfate and triethanolamine is used.
  g. a stiffening agent, preferably cetyl alcohol (hexadecanoic acid). Paraffin may also be used.
  h. an antimicrobial agent, preferably one or more parabens. The paraben may be methylparaben, propylparaben, ethylparaben, butyl paraben, or mixtures thereof. Other possible antimicrobial agents are imidurea, benzoic acid and benzoic alcohol.

A preferred formulation of the cream composition of the invention is:

| | |
|---|---|
| Cereal-derived β-D-glucan | about 0.5–15 w/w % |
| Petrolatum (white) | about 0.5–15 w/w % |
| Glycerol | about 5–15 w/w % |
| Propylene Glycol | about 2–6 w/w % |
| Cetyl Alcohol (Hexadecanoic Acid) | about 0.5–6 w/w % |

| -continued | |
|---|---|
| Triethanolamine | about 0.1–5 w/w % |
| Sodium Lauryl Sulfate | about 0.1–5 w/w % |
| Parabens | about 0.01–2 w/w % |
| Carrageenan | about 0.01–1.0 w/w % |
| Water | balance (at least 50%) |

A presently most preferred composition of the topical cream is as follows:

| | |
|---|---|
| Cereal-derived β-D-glucan | about 2 w/w percent |
| Petrolatum (white) | about 15 w/w percent |
| Glycerol | about 10 w/w percent |
| Propylene Glycol | about 4 w/w percent |
| Cetyl Alcohol (Hexadecanoic Acid) | about 2 w/w percent |
| Triethanolamine | about 2 w/w percent |
| Sodium Lauryl Sulfate | about 1 w/w percent |
| i-Carrageenan | about 0.3 w/w percent |
| Methyl Paraben | about 0.2 w/w percent |
| Propyl Paraben | about 0.2 w/w percent |
| Xanthan Gum | about 0.15 w/w percent |
| Water | balance (about 63.15 w/w %) |

Another preferred embodiment of the cream composition is as follows:

| | |
|---|---|
| Cereal-derived β-D-glucan | about 2 w/w percent |
| Petrolatum (white) | about 15 w/w percent |
| Glycerol | about 10 w/w percent |
| Propylene Glycol | about 4 w/w percent |
| Cetyl Alcohol (Hexadecanoic Acid) | about 2 w/w percent |
| Triethanolamine | about 2 w/w percent |
| Sodium Lauryl Sulfate | about 1 w/w percent |
| Parabens | about 0.25 w/w percent |
| Carrageenan | about 0.1 w/w percent |
| Water | balance (about 62.75 w/w %) |

EXAMPLE A

A 100 g batch of a topical cream of the invention was prepared having the following ingredients, given as g per 100 g total cream composition:

| | |
|---|---|
| Water | 63.15 g/100 g |
| White Petrolatum, m.p. 38–60° C. | 15.0 g/100 g |
| Glycerol | 10.0 g/100 g |
| Propylene Glycol | 4.0 g/100 g |
| Cereal (oat)-derived β-D-glucan | 2.0 g/100 g |
| Cetyl Alcohol | 2.0 g/100 g |
| Triethanolamine | 2.0 g/100 g |
| Lauryl sulfate | 1.0 g/100 g |
| i-Carrageenan | 0.3 g/100 g |
| Methylparaben | 0.2 g/100 g |
| Propylparaben | 0.2 g/100 g |
| Xanthan Gum | 0.15 g/100 g |

A stock solution of 4% β-D-glucan was prepared by dissolving 4.0 g of purified oat-derived β-D-glucan (powder) in 96 ml of distilled water in an autoclave bottle. The solution was stirred vigorously and then autoclaved at 121° C. with stirring until the glucan was fully dissolved.

To 50 ml of the stock solution of dissolved β-D-glucan were added the remaining ingredients at the above indicated weights. Additional water was added to bring the components of the mixture to the desired final concentrations. The mixture (at 85–90° C.) was liquified with constant stirring until all ingredients were dissolved and the mixture was homogeneous. The solution was then homogenized in a Polytron homogenizer for 45 seconds at a speed setting of 3.

The once-homogenized cream composition was cooled to about 50° C. and homogenized a second time at the same speed and time conditions. The cream composition was then dispensed into individual containers and cooled to room temperature.

When topically applied, the cream composition had a desired tactile soothing, non-greasy feeling with a consistency like that of whipped cream. The cream composition provided very good skin moisturization and emollience.

Alternatively, a fat free, water soluble version of the cream may be provided. In such a composition, the levels of Beta D-glucan and the other water soluble components world be increased, and no petrolatum base would be present. The concentration ranges from the examples given above would remain applicable.

A useful gel composition of the invention, including the active ingredient, cereal-derived β-D-glucan, is as follows:

| | |
|---|---|
| Cereal-derived β-D-glucan | about 0.5–15% |
| Water | about 80–98% |
| Polyvinyl alcohol | about 0.5–4% |
| Xanthan gum and/or CMC | about 0.5–4% |
| Other suspending agent(s) | about 0–4% |
| Antimicrobial agent(s) | about 0.1–1% |

Other suspending/viscosity increasing agent(s) which may be added include carrageenan, agarose, alginate, Carbomer 940™ thickener, and guar gum, at concentrations of each additional agent at about 0.01–4%. The use of xanthan gum and/or CMC is particularly advantageous for producing a clear colorless gel.

In addition, one or more emulsifying/solubilizing agents such as triethanolamine may be added at about 2 percent each.

Furthermore, a chelating agent such as ethylenediaminetetraacetic acid (EDTA) may be added at about 0.1–0.5 percent, generally as its tetrasodium salt.

Thus, a most preferred embodiment of the gel composition comprises:

| | |
|---|---|
| Cereal-derived β-D-glucan | about 2.0 w/w % |
| Polyvinyl alcohol | about 2.0 w/w % |
| Triethanolamine | about 2.0 w/w % |
| Carboxymethylcellulose (CMC) | about 2.0 w/w % |
| Additional suspending agent | about 0–4 w/w % |
| EDTA | about 0.2 w/w % |
| Methyl Paraben | about 0.2 w/w % |
| Propyl Paraben | about 0.2 w/w % |
| Water (at least 80%) | balance |

A preferred additional suspending agent is Carbopol™ 940 carbomer, added at about 0.5 percent.

EXAMPLE B

A 100 g batch of a gel composition of the invention was prepared having the following ingredients:

| | |
|---|---|
| Water (distilled) | 92.9 g/100 g |
| Cereal (oat)-derived β-D-glucan | 2.0 g/100 g |
| Triethanolamine | 2.0 g/100 g |
| Carboxymethylcellulose (CMC) | 1.0 g/100 g |
| Polyvinyl Alcohol | 1.0 g/100 g |
| Carbopol ™ 940 carbomer(acrylic acid homopolymer) | 0.5 g/100 g |
| Ethylenediaminetetraacetic Acid (EDTA) | 0.2 g/100 g |
| Methylparaben | 0.2 g/100 g |
| Propylparaben | 0.2 g/100 g |

43.9 g of water (room temperature) was placed in a container and stirred rapidly to produce a vortex at the bottom of the container. The weighed-out carbomer was then sifted into the agitated water until it dissolved completely. The remaining dry ingredients were then added to the container while stirring to achieve a uniform mixture/solution. The appropriate quantity (50.0 g) of the cereal (oat)-derived β-D-glucan stock solution of Example A was added to the container, and the mixture was liquified at 85–90° C. with constant stirring until all ingredients were dissolved and the solution homogeneous. The gel composition was allowed to cool to room temperature, and dispensed into individual containers.

The gel composition produced by this method had a soothing feeling with high moisturizing and emollient properties.

An oil-based topical composition containing cereal-derived β-D-glucan may be formulated. In this composition, the solvent of the basic cream or gel formulation is changed to be primarily an oil or mixture of oils. The water content is reduced to compensate for the increased concentrations of oil(s). The other ingredients may remain the same or be varied as desired. In the oil composition, the solvent may comprise, for example, all oil(s), or a mixture of oil and water, where the oil fraction is generally greater than the water fraction.

However, the preferred forms of topical compositions for treatment of burns and wounds are, at this time, the cream and gel formulations.

In a method of the invention for management of burns and wounds, the composition may be topically applied to the area of damaged tissue. The glucan containing cream or (gel of the invention provides a soothing emmolient, moisturizing, anti-pruritic and biologically-derived dermal protection to assist during the skin's recuperative process.

The treatment comprises:
1. thorough cleansing of the burn area or site of tissue destruction;
2. liberal topical application of the topical composition to the affected area; and
3. repeated application of the composition until healing is complete.

The method is useful for management of scars due to burns, wounds or surgery, and the cream or gel is topically applied to the affected hypertrophic or keloid scar. The topical composition provides a more rapid healing of burns or wounds, moisturizing relief for dryness and skin irritation, and a reduction in pruritus. The active ingredient, cereal-derived β-D-glucan may also be a biological response modifier, i.e. a macrophage stimulator.

What is claimed is:

1. A method for treating burns and wounds and other skin loss injuries and conditions comprising the step of applying to the affected area of the skin of a patient a topical composition comprising cereal derived β-D-Glucan as an active ingredient to thereby stimulate an immune response in the cells in the affected area of the skin.

2. The method of claim 1 wherein the topical composition comprises one of a cream base, a gel base and an oil base.

3. The method of claim 1 wherein the cereal derived b-D-Glucan is derived from one of barley, oats, and wheat.

4. A method for treating burns and wounds and other skin loss injuries and conditions comprising the step of applying to the affected area of the skin of a patient a topical composition comprising cereal derived β-D-Glucan characterized as (1→3) (1→4) β-D-Glucan as the active ingredient.

5. A method for treating burns and wounds and other skin loss injuries and conditions comprising the steps of:
   cleansing thoroughly a wound area of damaged tissue;
   applying to the wound area a topical composition comprising a cereal derived β-D-Glucan as the active ingredient to thereby stimulate an immune response in the cells in the wound area; and
   repeating the application of the topical composition until healing is complete.

6. A method of treating burns and wounds and other skin loss injuries and conditions comprising the steps of:
   cleansing thoroughly a wound area of damaged tissue;
   applying a topical composition comprising a cereal derived β-D-Glucan characterized as (1→3)(1→4) β-D-Glucan as the active ingredient; and
   applying repeatedly the topical composition until healing is complete.

7. A method for treating burns and wounds and other skin loss injuries and conditions comprising the steps of:
   cleansing thoroughly a wound area of damaged tissue;
   applying to the wound area a topical composition comprising a cereal derived β-D-Glucan as the active ingredient to thereby stimulate an immune response in the cells in the wound area; and
   repeating the application of the topical composition.

8. A method of treating burns and wounds and other skin loss injuries and conditions comprising the steps of:
   cleansing thoroughly a wound area of damaged tissue;
   applying a topical composition comprising a cereal derived β-D-Glucan characterized as (1→3)(1→4) β-D-Glucan as the active ingredient; and
   repeating the application of the topical composition.

* * * * *